US005817666A

United States Patent [19]
Katz

[11] Patent Number: 5,817,666
[45] Date of Patent: Oct. 6, 1998

[54] DERMATOLOGICAL PREPARATION AND METHOD FOR TREATING ACTINIC KERATOSES USING 5-FU

[76] Inventor: Bruce E. Katz, 14 E. 82nd St., New York, N.Y. 10028

[21] Appl. No.: 800,255

[22] Filed: Feb. 13, 1997

Related U.S. Application Data

[63] Continuation of Ser. No. 421,674, Apr. 12, 1995, Pat. No. 5,627,187.

[51] Int. Cl.$^6$ .................................................. A61K 31/505
[52] U.S. Cl. ........................... 514/274; 514/271; 514/859
[58] Field of Search ..................................... 514/859, 274, 514/271

[56] References Cited

U.S. PATENT DOCUMENTS 4,234,599  11/1980  Van Scott et al. ....................... 424/279

*Primary Examiner*—Theodore J. Criares
*Attorney, Agent, or Firm*—Gifford, Krass, Groh, Sprinkle, Patmore, Anderson & Citkowski, P.C.

[57] ABSTRACT

A composition for the treatment of actinic keratoses includes 5-fluorouracil and an alpha hydroxy carboxylic acid. The composition may further include ancillary ingredients. A therapeutic method involving the composition and a kit for carrying out the treatment are also disclosed.

17 Claims, No Drawings

DERMATOLOGICAL PREPARATION AND METHOD FOR TREATING ACTINIC KERATOSES USING 5-FU

This is a continuation of application Ser. No. 08/421,674 filed on Apr. 12, 1995, now U.S. Pat. No. 5,627,187.

FIELD OF THE INVENTION

This invention relates generally to methods and compositions for the treatment of skin. More particularly, the invention relates to methods and compositions for treating actinic damage to the skin. Most particularly, the invention relates to a composition including an antimetabolite material such as 5-fluorouracil in combination with a superficial skin peeling agent, and its use for reducing pre-malignant actinic keratoses.

BACKGROUND OF THE INVENTION

Skin cancer is the most common form of cancer seen in the world today. The three most common types of skin cancer include basal cell carcinoma (BCE), squamous cell carcinoma (SCC), and malignant melanoma (MM). One in five Americans will develop some form of skin cancer at some point in their lives, and it is estimated that over one million Americans will develop some form of skin cancer each year. Malignant melanoma is one of the deadliest types of cancer and has been increasing at an alarming rate. In just the last decade, its instance has doubled and it is predicted that one in 105 Americans will fall victim to this disease.

Sun exposure has been implicated in the etiology of BCE, SCC and MM. The epidemic rise in the rate of these cancers is thought to be directly related to substantial increases in our population's outdoor activities and the desire, over the past several decades, for a "tanned" skin appearance. Pre-malignant, actinic keratoses are common skin growths believed to be induced by solar exposure, and have the potential for developing into skin cancer in upwards of 20% of cases. They often appear on the skin years before the development of cutaneous carcinomas. Malignant melanoma often develops in areas of the body where there has been previous solar damage.

It is considered a standard of care to eradicate as many actinic keratoses as possible with the least amount of discomfort, inconvenience and trauma (morbidity), for the patient. Since it has been shown that the total number of actinic keratoses increases if left untreated, any therapy that produces a statistically significant decrease in their number would be considered effective treatment.

Surgical removal of actinic keratoses is not always possible or desirable. Surgery is not practical when many small keratoses are present, and the scarring produced by surgery is generally unacceptable for exposed, relatively visible areas of the skin. Furthermore, it is believed that, in the early stages of their development, many keratoses are very small so as to be invisible to the naked eye and hence difficult or impossible to remove surgically.

Topically applied, chemical agents such as 5-fluorouracil (5-FU) or masoprocol have been employed to eradicate actinic keratoses. While 5-FU has demonstrated efficacy for this purpose, it has been found to cause pain, itching, skin inflammation, ulceration and cosmetic disfigurement often so severe that patients must avoid being seen in public, because their appearance may cause fear or revulsion, thus making its therapeutic use unacceptable to many individuals. These effects also preclude the use of 5-FU over large areas of the skin to treat incipient and/or microscopic keratoses. Problems associated with the use of 5-FU have been recognized in the prior art, and U.S. Pat. No. 4,234,599 discusses the problems of 5-FU therapy and proposes the use of certain carboxylic acids, (particularly hydroxy acids and keto acids) as well as their esters and amine salts as substitutes for 5-FU in the treatment of actinic as well as non-actinic keratoses.

Various carboxylic acid compounds, particularly the halogenated carboxylic acids, the keto acids and the alpha hydroxy carboxylic acids, and especially glycolic acid and lactic acids, (as well as their esters, salts and lactones), are widely used at present as superficial skin peeling agents. It has been found that their use can produce cosmetic improvements in the appearance of the skin, but they have not been very effective in removing actinic keratoses.

It will thus be appreciated that there is a need for a topically active agent which is effective in removing actinic keratoses, while avoiding the undesirable side effects of prior art preparations. The present invention provides a composition which effectively removes actinic keratoses without severe side effects. The composition may be applied to relatively large areas of skin to treat macroscopic keratoses and to prevent the development of incipient keratoses. These and other advantages of the present invention will be readily apparent from the discussion, description and examples which follow.

BRIEF DESCRIPTION OF THE INVENTION

There is disclosed herein a composition for the treatment of actinic skin damage which comprises, by weight, about 0.10–10% an antimetabolite such as 5-fluorouracil and about 5–70% of a superficial dermal peel agent selected from the group consisting of: hydroxy carboxylic acids, keto acids, halogenated carboxylic acids, salicylic acid, and combinations thereof, disposed in a pharmaceutically acceptable carrier. The acid may, in some instances be present as a salt, ester, or lactone. In one embodiment of the invention, the composition includes approximately 5% 5-fluorouracil. In some instances, the superficial dermal peel agent comprises an alpha hydroxy acid, and in particular formulations, the acid comprises glycolic or lactic acid. The carrier may comprise a lotion, a gel or an aqueous carrier.

In accord with the present invention, there is also provided a method for the treatment of actinic skin damage comprising applying the composition of the present invention to the skin. The components of the composition may be applied together or in separate steps. In one particular method, the composition is applied to the skin and left on for about eight to 24 hours, after which it is rinsed off. In a particular variation of this therapy, the composition is applied to the skin once a week for about four to twelve weeks.

DETAILED DESCRIPTION OF THE INVENTION

The present invention is directed to a dermatological composition which effectively removes actinic keratoses while minimizing adverse effects generally encountered when using compositions of the prior art. The composition of the present invention includes 5-fluorouracil together with a superficial dermal peeling agent of the type generally employed for producing cosmetic enhancement of the skin by removing or minimizing wrinkles, photoaged skin, hyperpigmentation and the like. Such superficial peeling agents typically include organic acids, particularly halogenated acids, hydroxy acids and keto acids as well as phenol acids such as salicylic acid. The acids may be present in the free form, or as a salt, ester, lactone anhydride or other such derivative thereof, and within the context of this disclosure, "carboxylic acids" shall refer to the free acids as well as their derivatives. U.S. Pat. Nos. 4,234,599; 4,197,316; 4,363,815 and 5,091,171; the disclosures of which are incorporated herein by reference disclose carboxylic acids and their derivatives which have utility as superficial peel agents, and such materials may be used in the practice of the present invention. Alpha hydroxy acids (AHAs) are widely used as superficial peel agents, and glycolic acid and lactic acid are the most commonly employed.

The results obtained with the present invention are unexpected given the fact that 5-fluorouracil has been found to cause burning, itching, ulceration and other such skin damage; and superficial dermal peel agents, while only moderately irritating to the skin, are generally ineffective in removing keratoses.

It is known that AHAs and other such agents exert a superficial peel effect by increasing the permeability, and decreasing the adhesion of, the corneocyte layer of he skin. While not wishing to be bound by speculation, it is postulated that when 5-FU and superficial peel agents are combined in a single composition, the destructive effect of 5-FU on actinic keratoses is amplified due to its increased absorption through the more permeable corneocyte layer. Furthermore, photo damage at the level of the dermal elastic fibers is reduced, and in some instances reversed by the regenerative effect of the superficial peel agent. Therefore, through the use of the composition of the present invention premalignant actinic keratoses and other such solar damage are removed together with cosmetic lesions such as wrinkles and pigmentation. As a result, there is provided a composition in which the beneficial effect of the 5-FU is enhanced, by the increase in permeability and desquamation resultant from the presence of the superficial peel agent, so that lower concentrations thereof will suffice; furthermore, the restorative effect of the superficial peel agent counteracts any damage resultant from the 5-FU in an unexpected and beneficial manner.

In general, the active component of the composition of the present invention consists of between about .10–10% of an antimetabolite chemotherapeutic agent which is most preferably 5-FU and between about 5–70% the superficial peel agent, which is most preferably an alpha hydroxy carboxylic acid, it being understood that all percentages stated herein are weight percentages. The composition is typically disposed in a pharmaceutically acceptable carrier, of the type well known in the art and may further include other ingredients such as local anesthetics, humectants, colorings, fragrances, thickeners and the like.

In one particularly preferred embodiment, the 5-FU is present in a concentration of about 2–8% and even more preferably about 2–5%. As noted above, the carrier may further include humectants, fragrances, colors, thickeners, lubricants and preservatives, as is well known in the art. One particularly preferred humectant comprises a collagen derived material such as collagen laurate or the like. In some instances, the carrier may simply comprise water, whereas in other instances it may be a lotion based carrier and may typically include ingredients such as glycerine, propylene glycol, methyl and/or propyl paraben, hydroxyalkyl cellulose and the like. In one preferred embodiment, the carrier may comprise a hypo-allergenic, high lipid, cream based carrier.

EXPERIMENTAL

A clinical study was conducted to evaluate the effectiveness of one particular composition of the present invention. In the study, 20 patients, each having multiple, facial actinic keratoses were selected. One side (selected randomly) of each patient's face was treated with a composition of the present invention, and the other side treated with a prior art composition. Efficacy of the treatment was assessed on the basis of reduction in keratoses. Specifically, the prior art composition which was evaluated was Jessner's solution, a superficial facial peel composition known in the art and comprised of 14 grams of resorcinol, 14 grams of salicylic acid and 14 ml of lactic acid in 100 ml of 95% ethanol. The composition of the present invention comprised the Jessner's solution together with 5% 5-FU.

Patients were treated on a weekly basis, for eight weeks. At the beginning of each treatment, acetone was used to cleanse the entire face, after which the Jessner's solution was applied to both sides of the face, and the 5-FU composition of the present invention to one side. After each treatment patients were told not to wash their faces until the next morning. Beginning the day after treatment, subjects applied an emollient daily to prevent dryness. One recommended emollient comprised Ponds® skin smoothing capsules.

Prior to commencement of treatment, a baseline evaluation of keratoses was made for each patient. Facial photographs were taken at baseline and were repeated six months after termination of the study.

Table 1 represents a compilation of the data from the study. The table lists the number of keratoses on each side of the patient's face both before and after treatment and summarizes the percent of keratoses cleared during the treatment. It will be noted from the table that the composition of the present invention produced an 88% removal of keratoses whereas the Jessner's solution alone produced only a 15% removal. It is notable that in a number of instances, the solution of the present invention provided a 100% removal whereas the Jessner's solution alone provided no reduction in some instances.

In addition to the foregoing, skin biopsies were taken from three patients, both before treatment and six months after cessation of treatment. The biopsies were taken from an area approximately one centimeter anterior to the tragus on both sides of the face. In the skin taken from the side of the face treated with the 5-FU solution, it was noted that there was less epidermal dysplasia as compared to the side of the face treated with the Jessner's solution alone. In one case, improvement in dermal solar elastosis was noted in the half treated with the 5-FU composition.

Subjective global assessments by both the investigators and patients were all more positive for the 5-FU treatment than for the Jessner's solution. It was found there was a greater reduction in the number of solar lentigines, telangiectasias and rhytides on the halves of the face treated with the 5-FU solution. Complications occurring in the study were minimal and transient. Slight facial erythema and mild xerosis were occasionally noted. These problems resolved with the use of the emollient.

In summary, it was found that an eight week treatment with the composition of the present invention significantly reduced the number of actinic keratoses in the sample of patients. Adverse effects from the treatment were minimal, and the removal was permanent.

TABLE 1

| | NUMBER OF ACTINIC KERATOSES | | | | | |
|---|---|---|---|---|---|---|
| | BEFORE TREATMENT | | SIX MONTHS AFTER TREATMENT | | % OF ACTINIC KERATOSES CLEARED | |
| PATIENT NO | 5-FU + JESS | JESS | 5-FU + JESS | JESS | 5-FU + JESS | JESS |
| 1 | 8 | 11 | 0 | 10 | 100 | 9 |
| 2 | 19 | 22 | 1 | 15 | 95 | 32 |
| 3 | 15 | 7 | 2 | 5 | 87 | 29 |
| 4 | 8 | 7 | 1 | 7 | 88 | 0 |
| 5 | 13 | 17 | 3 | 11 | 77 | 35 |
| 6 | 11 | 9 | 1 | 8 | 91 | 11 |
| 7 | 21 | 28 | 3 | 27 | 86 | 4 |
| 8 | 10 | 11 | 0 | 7 | 100 | 36 |
| 9 | 8 | 7 | 1 | 5 | 88 | 29 |
| 10 | 18 | 27 | 5 | 25 | 72 | 7 |
| 11 | 9 | 12 | 1 | 11 | 89 | 8 |
| 12 | 14 | 15 | 0 | 15 | 100 | 0 |
| 13 | 12 | 10 | 1 | 9 | 92 | 10 |
| 14 | 13 | 11 | 2 | 8 | 85 | 27 |
| 15 | 14 | 16 | 3 | 15 | 79 | 6 |
| 16 | 18 | 16 | 3 | 15 | 83 | 6 |
| 17 | 14 | 12 | 2 | 10 | 86 | 17 |
| 18 | 9 | 8 | 0 | 6 | 100 | 25 |
| 19 | 14 | 11 | 1 | 11 | 93 | 0 |
| 20 | 8 | 10 | 2 | 9 | 75 | 10 |
| Average | 13 | 13 | 2 | 11 | 88 | 15 |

KEY:
5-FU + JESS = Half of Face Treated with 5-FU and Jessner's Solution Peel
JESS = Half of Face Treated with Jessner's Solution Peel Alone While the clinical study described above used 5-FU and Jessner's solution, a standard superficial peeling agent, similar beneficial results will be obtained using other superficial peel agents in combination with 5-FU. Other particularly preferred superficial peel agents include glycolic acid solutions and lactic acid solutions used either separately or in combination.

The concentration of 5-FU employed will depend upon the progress of the keratoses and the stage of treatment. Relatively higher 5-FU concentrations, i.e. about 5–10% will typically be employed for the removal of established keratoses. Somewhat lower concentrations, i.e., about 3–5%, may be employed to complete removal once it has begun, or in those instances where the higher concentrations are not tolerated by the patient. Still lower concentrations, i.e., about .10–1% may be employed as part of a post-removal maintenance program, or as a prophylactic treatment. Prophylactic treatment may further involve compositions including antioxidants, free radical scavengers, sun blocks and the like. Within the context of the present invention, variations in concentration of the active ingredients may be readily adjusted by a skilled practitioner to suit particular circumstances.

The composition of the present invention is most preferably used in a program of treatment wherein a series of applications are made to a patient's skin over a period of time. Most preferably, the treatment proceeds in a pulse mode, wherein the composition is applied to skin in a regular, though not daily, basis. Most preferably, treatment is carried out on a weekly basis. It has been found that pulse treatment produces a maximum effect with a minimum of discomfort to the patient. However, within the context of the present invention, it will be appreciated that treatment can also be carried out on a daily basis, especially when compositions including lower amounts of 5-FU are employed.

In general, it has been found to be most convenient to combine the superficial peel agent and the 5-FU in a single composition; however, in accord with the present invention, the two components may be applied sequentially without loss of effect. In such a sequential application, the two components may be applied in any order. It is generally preferred that the applications be made within about three to four hours of one another. More preferably, the applications are made within one hour and most preferably, they are made within about one half hour.

In some instances, such separate application will be an advantageous option when treatment is carried out in a physician's office. For example, a stock solution of superficial peel agent, typically about a 10% concentration agent may be first applied to the skin, and shortly thereafter the 5-FU containing composition applied. This mode of treatment will allow a physician to more easily adjust 5-FU concentration to a particular patient's needs.

Typically, the treatment methodology of the present invention will be carried out over a period of time, utilizing decreasing concentrations of active materials. Accordingly, the present invention may be implemented in connection with a treatment kit. The kit includes a series of compositions having different concentrations of 5-FU, typically ranging from about .10–10%. The kit will also preferably include materials for patient follow up such as emollients and skin conditioning agents such as alpha hydroxy acid containing compositions, antioxidants, free radical scavengers and the like.

Separate kits may be provided for use by physicians and patients. The physician's kit will include relatively high concentration 5-FU materials. In some embodiments, the physician's kit may include a stock solution of the superficial peel agent of approximately 10% concentration, and a number of separate containers of 5-FU at different concentrations. This will allow the physician to formulate specific concentrations for particular patients.

While the present invention has been described primarily with reference to the use of 5-FU as an active material, it will be appreciated that other similar agents will be apparent of one of skill in the art and therefore, the present invention may be practiced in connection with other materials having a mode of action similar to 5-FU. Such materials will most typically comprise other antimetabolites of nucleic acids. It is also to be understood that while the superficial peel agents are primarily described as carboxylic acids, it is to be understood that these acids may be present as their salts, esters, lactones, anhydrides, peroxides or other such derivatives.

The foregoing discussion and examples are meant to illustrate particular embodiments of the present invention and are not meant to be limitations upon the practice thereof. In view of the foregoing, numerous modifications and variations of the invention will be apparent to one of skill in the art. It is the following claims, including all equivalents, which define the scope of the invention.

I claim:

1. A composition for the treatment of actinic skin damage, said composition comprising by weight synergistic effective amounts of:
    about 0.10–10% 5-fluorouracil;
    about 5–70% of a superficial dermal peel agent selected from the group consisting of: hydroxy carboxylic acids, halogenated carboxylic acids, keto acids, salicylic acid, and combinations thereof; and
    a pharmaceutically acceptable carrier.

2. A composition as in claim 1 wherein said 5-fluorouracil is present at a concentration of about 2–5%.

3. A composition as in claim 1, wherein said superficial dermal peel agent comprises a free carboxylic acid.

4. A composition as in claim 1, wherein said superficial dermal peel agent comprises a derivative of a carboxylic acid.

5. A composition as in claim 4, wherein said derivative is selected from the group consisting of: esters, salts, lactones, anhydrides, and peroxides.

6. A composition as in claim 1, wherein said superficial dermal peel agent is an alpha hydroxy carboxylic acid.

7. A composition as in claim 6, wherein said alpha hydroxy carboxylic acid is selected from the group consisting of glycolic acid, lactic acid, and combinations thereof.

8. A method for the low morbidity treatment of skin conditions, said method comprising the steps of:

applying to the skin a composition comprising synergistically effective amounts of 0.1 to 10% by weight of 5-fluorouracil, and 5 to 70% by weight of a superficial dermal peel agent to the skin.

9. A method as in claim 8, wherein said superficial dermal peel agent is applied to said skin concomitant with the application of the 5-fluorouracil.

10. A method as in claim 8, wherein the superficial dermal peel agent is applied to the skin before the application of the 5-fluorouracil thereto.

11. A method as in claim 8, wherein the superficial dermal peel agent is applied to the skin after the 5-fluorouracil is applied thereto.

12. A composition for the treatment of actinic skin damage, said composition consisting essentially of, on a weight basis synergistic effective amounts of:

about .10–10% of 5-fluorouracil;

about 5–70% of glycolic acid or lactic acid; and a pharmaceutically acceptable carrier.

13. A kit for the treatment of actinic skin damage, said kit comprising:

at least two skin treatment compositions, each composition comprising by weight: about .10–10% 5-Fluorouracil, about 5–70% of a superficial dermal peel agent selected from the group consisting of: hydroxy carboxylic acids, halogenated carboxylic acids, keto acids, salicylic acid, and combinations thereof, and a pharmaceutically acceptable carrier, said at least two compositions further characterized in that the concentration of 5-Fluorouracil in each differs.

14. A kit as in claim 13, further including a cleanser for cleaning a patient's skin in preparation for application of one of said at least two compositions thereto.

15. A kit as in claim 14, wherein said cleanser comprises an absorbent pad saturated with a cleaning solution.

16. A kit as in claim 13, further including at least one applicator for applying said composition to a patient's skin.

17. A kit as in claim 13, further including a skin conditioning agent selected from the group consisting of emollients, antioxidants, free radical scavengers, superficial dermal peel agents and combinations thereof.

* * * * *

UNITED STATES PATENT AND TRADEMARK OFFICE
CERTIFICATE OF CORRECTION

PATENT NO. : 5,817,666
DATED : October 6, 1998
INVENTOR(S) : Bruce E. Katz

It is certified that error appears in the above-identified patent and that said Letters Patent is hereby corrected as shown below:

Column 7, Claim 8, Line 22 - Insert - - , said superficial dermal peel agent being selected from the group consisting of: hydroxy carboxylic acids, halogenated caboxylic acids, keto acids, salicylic acid and combinations thereof - - , after the word "skin."

Column 8, line 10 - Insert - - synergistic effective amounts of - - , after the word "weight."

Signed and Sealed this

Eleventh Day of May, 1999

*Attest:*

Q. TODD DICKINSON

*Attesting Officer*     *Acting Commissioner of Patents and Trademarks*